US008268770B2

(12) United States Patent
Privitera et al.

(10) Patent No.: US 8,268,770 B2
(45) Date of Patent: *Sep. 18, 2012

(54) FIBROUS SUBSTRATE WITH A SOLID HYPOHALITE PRECIPITATE FORMED THEREIN AND PROCESS OF MAKING

(75) Inventors: Marc P. Privitera, Walnut Creek, CA (US); William L. Smith, Pleasanton, CA (US); Edward Jason White, Pleasanton, CA (US); Leslie N. Adams, Manteca, CA (US)

(73) Assignee: The Clorox Company, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/016,555

(22) Filed: Jan. 28, 2011

(65) Prior Publication Data

US 2012/0141568 A1 Jun. 7, 2012

Related U.S. Application Data

(63) Continuation of application No. 12/960,297, filed on Dec. 3, 2010.

(51) Int. Cl.
C11D 11/00 (2006.01)
C11D 11/04 (2006.01)
C11D 3/395 (2006.01)
C11D 7/54 (2006.01)
C01B 11/06 (2006.01)

(52) U.S. Cl. ........ 510/438; 510/108; 510/379; 510/406; 510/439; 252/186.36; 252/186.37; 252/187.26; 252/187.27; 252/187.28; 252/187.3

(58) Field of Classification Search .................. 510/438, 510/439, 406, 108, 379; 252/186.36, 186.37, 252/187.26, 187.27, 187.28, 187.3
See application file for complete search history.

(56) References Cited

U.S. PATENT DOCUMENTS

| | | | |
|---|---|---|---|
| 4,513,459 A | 4/1985 | Doughty | |
| 4,857,292 A | 8/1989 | Brahm et al. | |
| 5,025,752 A | 6/1991 | Yananton | |
| 5,961,879 A | 10/1999 | Trigiante | |
| 6,562,016 B2 * | 5/2003 | Shinkai | 604/385.01 |
| 6,734,157 B2 | 5/2004 | Radwanski et al. | |
| 6,916,480 B2 | 7/2005 | Anderson et al. | |
| 7,008,600 B2 | 3/2006 | Katsigras et al. | |
| 7,204,931 B2 | 4/2007 | Martin et al. | |
| 7,540,056 B2 | 6/2009 | Dotterman et al. | |
| 7,638,470 B2 * | 12/2009 | Coke et al. | 510/109 |
| 7,647,890 B1 | 1/2010 | Yananton | |
| 2005/0107282 A1 * | 5/2005 | Ford et al. | 510/438 |
| 2005/0142157 A1 * | 6/2005 | Alimi | 424/405 |
| 2005/0155631 A1 * | 7/2005 | Kilkenny et al. | 134/6 |
| 2006/0168748 A1 | 8/2006 | Dotterman et al. | |
| 2006/0168750 A1 | 8/2006 | Dotterman et al. | |
| 2007/0238634 A1 * | 10/2007 | Foland et al. | 510/406 |
| 2008/0098546 A1 | 5/2008 | Warmka et al. | |
| 2008/0127994 A1 * | 6/2008 | Rippl et al. | 134/6 |
| 2010/0009889 A1 * | 1/2010 | Smith et al. | 510/379 |

* cited by examiner

Primary Examiner — Lorna M Douyon
(74) Attorney, Agent, or Firm — Erin Collins

(57) ABSTRACT

A cleaning substrate which comprises at least one layer of a solid hypohalite precipitate, wherein the hypohalite precipitate is formed in situ on the layer of substrate material. A process for making a fibrous cleaning substrate comprising the steps of: a) providing at least one layer of fibrous material; b) exposing the fibrous layer to an aqueous alkaline earth salt solution; c) treating the fibrous layer with a hypochlorite solution; d) allowing the aqueous alkaline earth salt solution combine with the hypochlorite solution to form a solid hypochlorite precipitate around the fibers in the fibrous material and a liquid phase, and e) removing at least 65% of the liquid phase from the fibrous substrate.

20 Claims, No Drawings

FIBROUS SUBSTRATE WITH A SOLID HYPOHALITE PRECIPITATE FORMED THEREIN AND PROCESS OF MAKING

CROSS-REFERENCE TO RELATED APPLICATIONS

This patent application is a continuation of copending U.S. patent application Ser. No. 12/960,297, filed Dec. 3, 2010.

BACKGROUND OF THE INVENTION

1. Field of the Invention

The present invention relates generally to a process for forming a solid hypochlorite precipitate on a fibrous substrate and the formed hypochlorite-releasing substrate. The process for forming a solid hypochlorite comprises the steps of: exposing one or more fibrous materials to an effective amount of aqueous alkaline earth salt solution, treating the fibrous material with an effective amount of hypohalite solution and allowing the alkaline earth salt solution to react with the hypohalite solution to form solid hypochlorite precipitate around the fibers in the fibrous material. The hypochlorite-releasing substrate may have a variety of uses, including but not limited to, cleaning wipes, dishwashing towels for hand use or in dishwashers, toilet bowl cleaning pads, bath and shower cleaning pads, laundry sheets for the washer or dryer, water filters, wound dressing materials, carpet stain removal pads, air deodorizer pads, food freshness substrates, air filtration substrates, and water disinfecting substrates. The composition and process for making the hypochlorite-releasing substrate enables the liquid phase to be removed from the substrate creating a stable hypochlorite-releasing substrate which is capable of rapid release of hypochlorite upon exposure to moisture or liquid.

2. Background of the Invention

There is a need for a stable cleaning and disinfecting substrate, such as a wipe or cleaning article that is capable of cleaning and removing residues from soiled surfaces while simultaneously destroying undesirable microorganisms, e.g. bacteria, mold, viruses, prions and the like that colonize on common surfaces with which people come into contact, such as door knobs, countertops, toilet seats, floors, beds, walls, and the like.

Hypohalite releasing compounds, such as the hypohalite and related compounds that release active forms of hypohalite and/or halogens, are extremely effective disinfectants capable of destroying a wide range of microorganisms. Hypohalite releasing antimicrobial compounds, and in particular the hypohalite, constitute a class of strong chemical oxidants possessing both cleaning and bleaching properties in addition to their antimicrobial properties making them superior to other disinfectants, such as quaternary ammonium biocides. The hypohalite class of chemical oxidants act to rapidly oxidize susceptible substances found in inorganic, organic and biological materials, rendering them more easily removed from surfaces, and in the case of colored or pigmented materials, bleaching them to white or colorless end products resulting in effective cleaning and stain removal from soiled surfaces. Owing to their strong oxidizing capability, hypohalite also posses inherent disinfection properties and additionally possess desirable characteristics including excellent aqueous solubility, mobility and a highly dissociative ionic nature. A further advantage of the hypohalite class with regard to disinfecting, is the speed and efficacy with which they attack microorganisms and either destroy them or render them non-viable following very short contact times. Yet a further advantage of the hypohalite is the wide susceptibility of many different types of microbial pests to their strong oxidizing potential and essentially the absence of any known microbe to develop an effective resistance against the action of these materials.

Typically, microbiologically contaminated surfaces seldom comprise only the microorganisms themselves, but include the presence of soils and other residues, including organic, inorganic and biological residues associated with the source of the microbiological contamination. These residues, including, for example, saliva, bodily is fluids, blood and common soils such as foods, oils and dirt, not only host microorganisms, but can act to shield and protect the microorganisms from the disinfectant action of non-hypohalite disinfectant materials.

One seeming disadvantage of the hypohalite class of materials is their susceptibility to decomposition, including self-decomposition and reactive decomposition owing to the interaction of the hypohalite with the substrates and materials, which they contact during packaging and storage. Particularly in the case of pre-wetted wipes, the disinfecting hypohalite composition is impregnated onto and interacts with the absorbent carrier substrate during storage. Hence, freshly prepared solutions or disinfectant articles utilizing these materials are typically required to ensure adequate activity for ensuring effective disinfection of surfaces. Attempts have been made in the past to provide a convenient disinfectant article by loading a liquid hypohalite solution onto an absorbent substrate such as a wipe. One of the problems with pre-loaded bleach wipes is that they lack sufficient stability to ensure suitable disinfecting efficacy at time of use, particularly following typical storage times and/or less than ideal storage conditions representative of real world environments encountered in the home, office, business, hospital or field where needed.

Another prior art embodiment of hypohalite loaded substrate which has been used previously is a dry substrate which is loaded with a solid hypohalite which is adhered to the substrate using a binder or adhesive agent. The problems with these dry loaded solid hypohalite substrates is that the solid hypohalite may only be loaded on the exterior of the surface of the substrate rather than evenly distributed throughout the substrate, the adhesive agent or binder may interferes with the quick release of the hypohalite, and if the particles size of the solid hypohalite is too large then the release rate may be too slow, but if the particles are too small the particles will fall off the substrate too easily and will not be delivered to the desired point of use.

3. Description of the Related Art

The prior art covers numerous types of cleaning substrates and compositions with hypochlorite. Wet cleaning wipes loaded with hypochlorite are know in the art and cleaning tools with pad loaded with a particulate hypochlorite which is adhered to the surface of the pad with a binder or adhesive are also well-known in the art. In addition, there are also solid tablets which include a solid hypochlorite which are commonly used in toilet bowl cleaning tablets. Furthermore, there are numerous processes for the formation of hypochlorite which are also described in the prior art. None of the prior art references describe a process for making a solid hypochlorite precipitate on a nonwoven substrate or a fibrous substrate where the solid hypochlorite is formed on the substrate as a precipitate.

U.S. Pat. No. 7,008,600 to Kastigras et al. discloses a cleaning composition containing hypohalite and surfactant on a nonwoven substrate forming a wet cleaning wipe or pad. In the case of the Kastigras invention, the cleaning composition with the hypohalite and surfactant is formed and then it is loaded onto the nonwoven substrate. In addition, the disinfecting article of Kastigras is in a wet form on the substrate and must be stored in a sealable housing to ensure the stability of the substrate with the hypohalite solution. Unlike the present invention, the disinfecting article taught by Kastigras contains a hypohalite cleaning composition that is formed prior to being added to the nonwoven substrate and the disinfecting article is loaded with an aqueous solution of hypohalite and surfactant. The use of a wet wipe loaded with an aqueous solution of hypochlorite is less desirable than having a wipe with the liquid phase removed because there are stability and degradation problems that necessitate the use of a sealable housing.

U.S. Pat. No. 6,916,480 to Anderson et al. describes a wipe with controlled-release of antimicrobial agents which may include calcium hypochlorite particles. Similarly, U.S. Pat. No. 6,734,157 to Radwanski, et al. teaches a controlled-release wipe which may contain calcium hypochlorite particles adhered to the surface of the wipe. The antimicrobial wipe taught by Anderson utilizes a polymer mixture to control the release rate of the antimicrobial agent loaded on the wipe. In the case of Anderson and Radwanski, the antimicrobial wipes are formed by adhering solid particles of calcium hypochlorite to the surface of the wipe with an adhesive or binding agent. Anderson does not teach a process for forming a solid hypochlorite precipitate on a fibrous material in the absence of a binder or adhesive. One of the deficiencies of this type of substrate where a solid bleach particle is adhered to the substrate is that the adhesive and/or the larger particle size prevent rapid release of the hypochlorite when it is exposed to moisture or liquid. If less adhesive is used or small particle size hypochlorite is used then there is a problem with dusting because the particles will not all stay on the substrate prior to use. In addition, the antimicrobial wipe taught by Anderson has solid hypochlorite particles on the surface of the wipe rather than solid hypochlorite precipitate formed around the fibers of the fibrous substrate, as in the present invention. In addition, the invention of Anderson requires that the hypohalite particles are on the surface of the wipe, whereas the present invention allows the hypohalite precipitate to be substantially evenly distributed throughout one or more layers of the substrate material.

The use of a particulate form of solid hypochlorite adhered to the surface of the substrate is less desirable than the present invention because a binder or adhesive is necessary which adds additional expense. In addition, to make the solid calcium hypochlorite particles adhere to the surface of the wipe they cannot be so fine that they fall off the surface of the substrate leading to dusting or exfoliation. Unfortunately, particles that are large enough to effectively adhere to the surface of the substrate means there is less surface area exposed to moisture or fluid which means a slower release rate of hypochlorite than that of the present invention.

U.S. Pat. No. 4,513,459 to Doughty describes a bleach cake in a filter sleeve which is used in toilet bowl tanks to clean and disinfect. The bleach cake in Doughty comprises a solid calcium hypochlorite and the filter sleeve surrounds the bleach cake to prevent particles from the cake breaking off and obstructing flow of the water into the toilet bowl from the tank. The invention of Doughty differs from the present invention because the bleach cake is formed as a separate solid material that is then encased in the filter sleeve whereas the present invention involves the formation of a solid hypochlorite precipitate around the fibers of a fibrous substrate.

The prior art references teach wet loaded hypochlorite containing wipes which have stability and degradation problems unless they are stored in sealable containers which do not allow light or air exposure. The prior art also teaches wipes loaded with solid particulate calcium hypochlorite particles using an adhesive or binder which have the added expense of an adhesive and do not release hypochlorite as efficiently as the present invention. In addition the prior art also teaches bleach cakes, but these bleach cakes are not formed on a fibrous substrate and are primarily a solid bleach rather than a combination of solid bleach and fibrous material. In addition, there are references about the formation of calcium hypochlorite but none which talk about hypochlorite formation on a fibrous substrate. In view of the prior art, there is a need for a process for forming a solid hypochlorite precipitate on a fibrous substrate and a hypochlorite releasing substrate that overcomes the disadvantages and shortcomings associated with prior art processes and hypochlorite releasing substrates.

SUMMARY OF THE INVENTION

The present invention relates to a hypohalite-releasing substrate comprising: a) at least one fibrous layer comprising fibers selected from the group consisting of: natural cellulose, regenerated cellulose, polyester, acrylic, nytril, cellulose ester, olefin, vinyl and any combinations or mixtures thereof, b) a solid hypohalite precipitate formed around the fibers and in the interstices of the fibrous layer selected from mixtures and combinations of hypohalite salts.

In one embodiment of the invention, the hypohalite-releasing substrate is a hypochlorite-releasing substrate and the hypohalite precipitate is a hypochlorite precipitate selected from the group consisting of: hypochlorite monohydrate salt, hypochlorite dihydrate salt, hemibasic hypochlorite salt, monobasic hypochlorite salt, dibasic hypochlorite salt, anhydrous hypochlorite salt, and mixtures and combinations thereof. In another embodiment of the invention, the substrate is substantially free of any glues, binders, adhesives, tackifying agents or the like. In another embodiment wherein the solid hypochlorite precipitate is uniformly distributed throughout the first fibrous layer. In another embodiment of the invention, the hypochlorite-releasing substrate is substantially dry-to-the-touch and the hypochlorite-releasing substrate comprises less than 35% of a liquid phase, preferably less than 25% of a liquid phase, more preferably less than 20% of a liquid phase or even less than 10% of a liquid phase.

The present invention also includes a process for forming a solid hypochlorite precipitate on a fibrous substrate and making hypochlorite-releasing substrate. The process of forming a solid hypochlorite precipitate on a fibrous substrate comprises the steps of: (a) providing at least one layer of fibrous material, (b) exposing the fibrous material to an effective amount of aqueous alkaline earth salt solution, (c) treating the fibrous layer with an effective amount of hypochlorite solution and, (d) allowing the aqueous alkaline earth salt solution to combine with the hypochlorite solution to form a solid hypochlorite precipitate around the fibers in the fibrous material. In one embodiment of the invention, the process for forming the solid hypochlorite precipitate on a fibrous substrate includes removing at least 65% the liquid phase from the substrate, preferably removing at least 75% or at least 80% or 90% of the liquid phase from the substrate. The liquid phase may be removed from the substrate by a heating, drying, evaporating, vacuum drying or stripping, or any other suitable method for removing liquid from the substrate.

In another embodiment of the invention, there are at least two fibrous materials wherein the first fibrous material is exposed to an alkaline earth salt solution and the second fibrous material is treated with a hypochlorite solution and then the first and second fibrous materials brought into contact with one another to cause the formation of a solid hypochlorite precipitate on the fibrous substrate. In this embodiment the substrate may contain two or more layers of fibrous materials. There may be additional layers of substrate material coating an alkaline solution, or a hypohalite solution, or additives such as surfactants, dyes, builders, pH adjustors, fragrances, abrasives, etc. There may also be additional layers of substrate materials which are fibrous or non-fibrous which may be un-loaded or loaded with additional cleaning compositions or additives.

In one embodiment, the hypochlorite-releasing fibrous substrate may be a cleaning wipe or pad. In another embodiment of the invention, the hypochlorite-releasing substrate may be a filtration device for cleaning and disinfecting water or air. In another aspect of the invention, the hypochlorite-releasing substrate may used for as a wound dressing. In another aspect of the invention, the hypochlorite-releasing substrate can be used as a source for generating bleach vapor. In one embodiment, the hypochlorite-releasing substrate may be used in conjunction with household appliances, including but not limited to, dishwashers, laundry machines, dryers, and/or vacuums to clean and disinfect various surfaces around the home.

The hypochlorite-releasing substrate may be created to provide a sufficient amount of active hypochlorite which remains effective for an extended period of time to reliably disinfect hard surfaces such as countertops, toilet seats, door knobs and the like commonly found in the home, hospital, food service and other industries. In another embodiment of the invention, the hypochlorite-releasing substrate may be loaded with relatively low levels of hypochlorite to provide a more mild solution which may be used for air or water sanitization or to clean soft surfaces without causing discoloration. The amount of solid hypochlorite precipitate on the fibrous substrate will depend on the desired application and use of the substrate.

Further features and advantages of the present invention will become apparent to those of ordinary skill in the art in view of the detailed description of preferred embodiments below, when considered together with the attached claims.

DETAILED DESCRIPTION OF THE INVENTION

Before describing the present invention in detail, it is to be understood that this invention is not limited to particularly exemplified systems or process parameters that may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to a "salt" includes two or more such salts.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

The "hypohalite-releasing substrate" or "hypochlorite-releasing substrate" can be used as a disinfectant, sanitizer, and/or sterilizer. As used herein, the term "disinfect" shall mean the elimination of many or all pathogenic microorganisms on surfaces with the exception of bacterial endospores. As used herein, the term "sanitize" shall mean the reduction of contaminants in the inanimate environment to levels considered safe according to public health ordinance, or that reduces the bacterial population by significant numbers where public health requirements have not been established. An at least 99% reduction in bacterial population within a 24 hour time period is deemed "significant." As used herein, the term "sterilize" shall mean the complete elimination or destruction of all forms of microbial life and which is authorized under the applicable regulatory laws to make legal claims as a "Sterilant" or to have sterilizing properties or qualities.

In the application, effective amounts are generally those amounts listed as the ranges or levels of ingredients in the descriptions, which follow hereto. Unless otherwise stated, amounts listed in percentage ("%'s") are in weight percent (based on 100% active) of the cleaning composition alone, not accounting for the substrate weight. Each of the noted cleaner composition components and substrates is discussed in detail below.

As used herein, the terms "fibrous substrate", "fibrous layer" and "fibrous materials" are intended to include any material that that is formed of fibers. Examples of fibrous substrates include, but are not limited to nonwovens, sponges, wipes, pads, filtration devices, laundry sheets, bandages, fiber strands, cleaning heads and similar materials which can be attached to a cleaning implement, such as a floor mop, handle, or a hand held cleaning tool, such as a toilet cleaning device.

As used herein, "disposable" is used in its ordinary sense to mean an article that is disposed or discarded after a limited number of usage events, preferably less than 25, more preferably less than about 10, and most preferably less than about 2 entire usage events.

As used herein, "fibers" included hypochlorite stable fibrous materials, including but not limited to, natural cellulose, regenerated cellulose, polyester, acrylic, nytril, cellulose ester, olefin, vinyl and any combinations or mixtures thereof. In one embodiment of the invention, the fibrous material comprised fibers selected from the group consisting of: polypropylene, polyethylene, polyester and mixtures and combinations thereof including bicomponent and multicomponent fibers.

As used herein, "wiping" refers to any shearing action that the substrate undergoes while in contact with a target surface. This includes hand or body motion, substrate-implement motion over a surface, or any perturbation of the substrate via energy sources such as ultrasound, mechanical vibration, electromagnetism, and so forth.

As used herein, the terms "nonwoven" or "nonwoven web" means a web having a structure of individual fibers or threads which are interlaid, but not in an identifiable manner as in a knitted web. Nonwoven webs have been formed from many processes to form materials, such as, for example, spunbond, meltblown, spunbond-meltblown-spunbond (SMS), carded, wetlaid, airlaid, thermalbonded, hydroentangled, through-air-bonded, needled, chemical bonded and any combinations thereof.

As used herein, the term "solid hypohalite precipitate" generally includes a precipitate that is formed by the reaction of an effective amount of an aqueous alkaline earth salt solution and a hypohalite solution. The hypohalite precipitate may be hypohalite salt or a mixture or combination of various hypohalite salts. Similarly, the term "solid hypochlorite precipitate" generally includes a precipitate that is formed by the reaction of an effective amount of an aqueous alkaline earth salt solution and a hypochlorite solution. More specifically, the "solid hypochlorite precipitate" may be crystalline or amorphous and comprises one or more salts selected from the group consisting of: hypochlorite dehydrate salt, hemibasic hypochlorite salt, monobasic hypochlorite salt, dibasic hypochlorite salt, and any mixtures and combinations thereof.

The term "alkaline earth salt solution", as used herein, means a solution selected from the group consisting of: magensium chloride, calcium chloride, calcium hydroxide, magnesium hydroxide and mixtures thereof.

The term "hypochlorite solution", as used herein, is meant to mean a solution comprising compounds selected from the group consisting of: sodium hypochlorite, potassium hypochlorite, lithium hypochlorite, calcium hypochlorite, magnesium hypochlorite, hypochorlous acid and mixtures and combinations thereof.

The term "liquid phase", as used herein, refers to water, solvents and any other liquids that may be absorbed into the substrate material. In one embodiment of the invention, about 65% to 100% of the liquid phase is removed from the fibrous layer containing the hypohalite precipitate. The layer with the hypohalite precipitate may be substantially dry-to-the-touch after the removal of most of the liquid phase. In another embodiment of the invention, at least 65% of the liquid phase is removed from the entire substrate which may be one or more layers of material. This means that at least 65% of the liquid on the substrate which may be water, solvent, any other liquids or combinations thereof is removed from a single layer of fibrous material in the substrate, or multiple layers of substrate materials or then entire substrate.

The term "additive", as used herein, is meant to mean an optional ingredient to the composition, which included but is not limited to, emulsifiers, pH adjusters, silicones, surfactants, soil release agents, soil release polymers, antistatic agents, fragrances, fragrance extenders, antimicrobial additives, dyes, colorants, viscosity control agents, foaming agents, peralizing agents, opacifying agents, anitxoidants, sunscreens, dye transfer inhibitors, dye fixative agents, dispersants, chlorine scavengers, wetting agents, electrolytes, enzymes, brightners, heavy metal chelating agents, fabric softeners, soil suspending agents, thickeners and mixtures thereof. In a preferred embodiment of the present invention, it is preferred that any additives are hypochlorite stable.

The term "surfactant", as used herein, is meant to mean and include a substance or compound that reduces surface tension when dissolved in water or water solutions, or that reduces interfacial tension between two liquids, or between a liquid and a solid. The term "surfactant" thus includes anionic, nonionic and/or amphoteric agents.

The term "consisting essentially of" as used herein, limits the scope of a claim to the specified materials or steps "and those that do not materially affect the basic and novel characteristic(s)" of the claimed invention. In re Herz, 537 F.2d 549, 551-52, 190 USPQ 461, 463 (CCPA 1976) (emphasis in original). See MPEP 2111.03 For the purposes of searching for and applying prior art under 35 U.S.C. 102 and 103, absent a clear indication in the specification or claims of what the basic and novel characteristics actually are, "consisting essentially of" will be construed as equivalent to "comprising." See, e.g., PPG, 156 F.3d at 1355, 48 USPQ2d at 1355. See MPEP 2111.03

Processes for Making a Substrate with a Hypohalite Precipitate

The present invention relates to a process for creating a stable hypochlorite-releasing substrate which is substantially dry-to-the-touch and is substantially free of binders, adhesives, tackifying agents and the like. The method of the present invention involves forming a solid hypochlorite precipitate on a fibrous substrate material. The reaction used to form the solid hypochlorite precipitate is as follows:

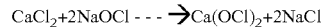

$$CaCl_2 + 2NaOCl \dashrightarrow Ca(OCl)_2 + 2NaCl$$

The process of forming a solid hypochlorite precipitate on a fibrous substrate comprises the steps of: (a) providing at least one layer of fibrous material, (b) exposing the fibrous material to an effective amount of aqueous alkaline earth salt solution, (c) treating the fibrous layer with an effective amount of hypochlorite solution and, (d) allowing the aqueous alkaline earth salt solution to combine with the hypochlorite solution to form a solid hypochlorite precipitate around the fibers in the fibrous material. In one embodiment of the invention, the process for forming the solid hypochlorite precipitate on a fibrous substrate includes removing at least 65% the liquid phase from the substrate. In another embodiment of the invention, at least 75% of the liquid phase is removed from the substrate, preferably removing at least 80% of the liquid phase from the substrate, more preferably removing at least 85% of the liquid phase from the substrate, and most preferably removing at least 90% of the liquid phase from the substrate. The liquid phase may be removed from the substrate by a heating, drying, evaporating, vacuum drying and/or stripping and any other suitable method or combination of methods for removing liquid from the substrate.

In one embodiment of the invention, the alkaline earth salt solution selected from the group consisting of: magnesium chloride, calcium chloride, calcium hydroxide, magnesium hydroxide and any mixtures or combinations thereof. In another embodiment, the hypochlorite solution comprises compounds selected from the group consisting of: sodium hypochlorite, potassium hypochlorite, lithium hypochlorite, calcium hypochlorite, magnesium hypochlorite, hypochlorous acid, and any mixtures of combinations thereof. In an alternative embodiment, the solid hypochlorite precipitate contains salts selected from the group consisting of: hypochlorite monohydrate salt, hypochlorite dihydrate salt, hemibasic hypochlorite salt, monobasic hypochlorite salt, dibasic hypochlorite salt, anhydrous hypochlorite salt, and mixtures and combinations thereof. The solid hypochlorite precipitate may be amorphorous or crystalline.

In one embodiment of the invention, a nonwoven substrate material is dipped and fully saturated with a calcium chloride solution. Concentrations of between about 10% to about 55% by weight are desirable for forming the calcium chloride solution. The active level of the calcium chloride solution may be used to control the loading level of the resulting solid hypochlorite precipitate desired on the substrate. The nonwoven substrate material is then dipped into or sprayed with a stochiometric amount of a sodium hypochlorite solution. The strength of the solution is dependent upon the desired level of water removal and the water absorption characteristics of the nonwoven substrate material. Optionally, the substrate may be sprayed with sodium carbonate and lauric acid.

In this embodiment of the invention, the nonwoven substrate may absorb between 10% and 1000% by weight of its own mass. The resulting loading ratio of substrate weight to liquid weight is about 0.1:1 to about 1:100, preferably about 0.1:1 to about 1:10, most preferably about 1:2 to about 1:8.

The formation of the solid hypochlorite precipitate from the two liquid reagents in the nonwoven substrate is fully incorporated into the nonwoven structure after at least 50% or more of the liquid phase is removed from the substrate by heating, drying, evaporation, etc. The concentration of the sodium hypochlorite solution will determine the amount of heating or drying time required to remove the excess liquid phase from the substrate. Sodium hypochlorite concentrations of about 1% to about 10% by weight are desirable. The ionic strength of the solution will drive the reaction rate. Equimolar salt solutions and higher ionic strength solutions are feasible using this process.

Additional layers of substrate materials may be included along with layer of substrate containing the hypochlorite precipitate. For example, another layer of nonwoven material comprising foaming surfactants or surfactant combinations such as: secondary alkyl sulfate (SAS) surfactants and amine oxide surfactants, caustic neutralized coco fatty acid, and caustic neutralized lauric acid. These foaming surfactant combinations are intended to be exemplary combinations, but they do not limit the possibilities of other suitable surfactants or combinations that may be more desirable for alternative cleaning compositions and cleaning substrates. The substrate layer comprising foaming surfactants may be embedded into the structure of the nonwoven substrate using liquid solutions that change phase with temperature or co-precipitate as a solid surfactant precipitate at the same time as the hypochlorite precipitate is being formed. The surfactant precipitate may be formed in situ on one of the layers of substrate material. The surfactant precipitate may be evenly distributed throughout the width and/or length of one or more fibrous layers of the substrate material. Alternatively, the solid surfactant precipitate may distribute only on the top of one or more of the fibrous layers. A substrate layer comprising foaming surfactants may be formed separately from the hypochlorite precipitate layer and then joined together once the hypochlorite precipitate layer is substantially dry.

The fibrous material may be exposed to the aqueous alkaline earth salt solution by a variety of different means, including but not limited to dipping, spraying, dosing, dripping, soaking, showering, misting, printing or any other suitable means for applying the aqueous alkaline earth salt solution to the fibrous substrate material. In one embodiment of the invention, the entire layer of fibrous material or entire multiple layers of fibrous materials are treated with the aqueous earth salt solution. In another embodiment of the invention, only portions of the layer of fibrous material are treated with the alkaline earth salt solution so that the treatment is not uniformly applied across an entire layer of the substrate material.

Similarly, the fibrous material may be treated with an effective amount of hypochlorite solution by a variety of different means, including but not limited to dipping, spraying, dosing, dripping, soaking, showering, misting, printing or any other suitable means for applying the hypochlorite solution to the fibrous substrate material. In one embodiment of the invention, the entire layer of fibrous material or entire multiple layers of fibrous materials are treated with the hypochlorite solution. In another embodiment of the invention, only portions of the layer of fibrous material are treated with the hypochlorite solution so that the treatment is not uniformly applied across an entire layer of the substrate material.

In another embodiment of the invention, at least one fibrous material may be treated with an effective amount of hypochlorite solution by a variety of different means, including but not limited to dipping, spraying, dosing, dripping, soaking, showering, misting, or any other suitable means for applying the aqueous alkaline earth salt solution to the fibrous substrate material. Then the fibrous material treated with an effective amount of hypochlorite solution is exposed to chlorine gas and some of the liquid phase is removed to create a soild hypochlorite precipitate on the fibrous substrate.

In another embodiment of the invention, there are at least two fibrous materials wherein the first fibrous material is exposed to an alkaline earth salt solution and the second fibrous material is treated with a hypochlorite solution and then the first and second fibrous materials brought into contact with one another to cause the formation of a solid hypochlorite precipitate on the fibrous substrate. In this embodiment the substrate may contain two or more layers of fibrous materials. There may be additional layers of substrate material coating an alkaline solution, or a hypohalite solution, or additives such as surfactants, dyes, builders, pH adjustors, fragrances, abrasives, etc. There may also be additional layers of substrate materials which are fibrous or non-fibrous which may be un-loaded or loaded with additional cleaning compositions or additives.

Substrate Materials

Suitable substrates may be provided by a variety of sources, including woven and non-woven webs, fabrics, foams, sponges, films and similar material constructs capable of being treated with an aqueous alkaline earth salt solution and with an effective amount of a hypochlorite solution. In one embodiment, films may be a suitable substrate. Suitable films may be perfereated and/or porous films or slit films which comprise flat fibers. In one embodiment, the substrate has a least one layer of fibrous material wherein the fibers are selected from the group consisting of: polypropylene, polyethylene, polyester and any mixtures or combinations thereof including bicomponent and multicomponent fibers. Additional layers of the substrate may comprise a wide variety of materials, including but not limited to, natural fibers, synthetic fibers, foams, abrasive materials, sponges, moisture impermeable materials or layers, and any combinations or permutations thereof. The subtrate may be a layered material with any combination of materials, including but not limited to, woven and non-woven webs, fabrics, foams, sponges, films and similar material constructs which are capable of carrying a solid hypochlorite precipitate.

In an alternate embodiment of the invention the treatment of the fibers with the hypochlorite solution and/or the alkaline earth salt solution may occur at the same time the fibers are being formed into a fibrous web. For example, as the fibers are being formed into a fibrous web they could pass through wet sections or treatment areas or processes where they are treated with an alkaline earth salt solution and then a second wet treatment where the fibers are treated with hypochlorite solution before or concurrently with the process of forming the fibers into a woven or non-woven substrate. Alternatively, fibers may be treated with an alkaline earth salt material and formed into a woven or non-woven substrate and then treated with a hypochlorite solution or chlorine gas. Similarly, fibers may be treated with a hypochlorite solution and formed into a woven or non-woven substrate and then treated with an alkaline earth salt solution. In another embodiment, a portion of the fibers may be treated with a hypochlorite solution and a portion of the fibers may be treated with an alkaline earth salt solution. When the treated hypochlorite fibers and the treated alkaline earth salt fibers are formed into the fibrous web the solid hypochlorite precipitate forms. In various embodiments of the invention, the solid hypochlorite precipitate therefore may be formed on individual fibers, on a fibrous web substrate, or on portions of a fibrous web substrate where the treated hypochlorite fibers and the treated alkaline earth salt fibers come into contact with one another.

In another embodiment of the invention, the substrate material is a film or resin that is extruded with the alkaline earth salt salt(s) already in the film or resin. The extruded fibers containing the alkaline earth salts can be treated with a hypochlorite solution or a chlorine gas. If a choline gas is used with the extruded fibers containing the alkaline earth salt(s) then the entire process is a dry process and therefore the additional step of removing the liquid phase is not necessary to form the solid hypochlite precipitate.

The substrate may comprise a single layer or multiple layers of one or more materials. The substrate may also comprise a combination of one or more materials and/or one or more forms of materials. The multiple layers or multiple forms of materials are bonded to each other by suitable means to prevent separation. For example, a sheet of one material may be combined with a second sheet of a second material and bonded together by suitable means. Suitable means of bonding sheets together includes, by way of example and not by way of limitation, hydroentangling, embossing, adhesion and heat or sonic welding. A further example, a non-woven sheet of one material may be combined with a second material formed into deformable and compressible foam, and bound together by a suitable means. In this manner, all conceivable combinations of materials may be combined to provide useful articles for a variety of cleaning and disinfecting requirements.

In one embodiment of the invention, the substrate comprises at least one layer of fibrous material which is a non-woven material selected from the group consisting of: spunbond, meltblown, SMS, carded, wetlaid, airlaid, thermalbonded, hydroentangled, through-air bonded, needled, chemical bonded, coform and combinations thereof. The substrate material which is loaded with the solid hypohalite precipitate may be formed on a layer of fibrous material which is already part of a single or multilayer substrate which is ready for use. Alternatively, the solid hypohalite precipitate may be formed on a layer of fibrous material that maybe later joined into a multilayer substrate or tool or may be additionally processed by adding texture, additives or other components to form a finished hypohalite-releasing article or tool.

In one embodiment, the substrates have a series of apertures, which improve substrate stability, because apertures can decrease the overall surface area by up to 20%. For cleaning wipes, the substrate is preferred to be in sheet form. Preferably, the cross-sectional thickness dimension of the substrate sheet is proportionally smaller than either its approximate width or length dimension in order to provide at least one surface whose surface area is sized appropriately with respect to the intended surface to be treated with the disinfectant article. The cleaning wipe substrate may be formed into individual sheets or wipes or as a continuous sheet. In continuous sheet form, it is preferred to provide means, such as partial tears or perforations across at least one dimension of the sheet, such that the continuous sheet may be subdivided prior to use to a suitable size for the particular need at hand.

The substrate may comprise a wipe, cleaning pad or cleaning head for a tool. The wipe or cleaning pad can be used with the hand, or as part of a cleaning implement attached to a tool or motorized tool, such as one having a handle. A hypohalite-releasing substrate used as a cleaning head with a tool may be particularly useful for cleaning bathtubs, toilets, showers, sinks, and other suitable household surfaces. Examples of tools using a wipe or pad include U.S. Pat. No. 6,611,986 to Seals, WO00/71012 to Belt et al., U.S. Pat. App. 2002/0129835 to Pieroni and Foley, and WO00/27271 to Policicchio et al.

Further, the substrate can be combined with non-absorbent materials, preferably in the form of films, sheets or blocks. Preferably, the non-absorbent materials are liquid impervious, in that they do not permit the passage of the hypohalite compositions which are released from the substrate in the presence of moisture or liquid. In one example, the non-absorbent materials may be bonded to one side of a suitable hypohalite-releasing substrate creating a layered substrate. The layered substrate has a liquid impervious barrier to prevent passage of the disinfectant composition from the absorbent material to the outside surface of the barrier material. Thus the liquid impervious barrier allows the user to handle the layered disinfectant article without direct contact with the disinfectant loaded side of the layered article. Another example is a thin liquid impervious plastic sheet bounded to a hypochlorite-releasing substrate layer, whereby the user contacts the plastic sheet during use rather than contacting the hypochlorite-releasing layer or layers of the substrate while wiping the surface to be treated.

According to the present invention, the substrate layers and materials may be produced by any method known in the art. For example, non-woven material substrates can be manufactured by dry forming techniques such as air laying or wet laying such as on a paper making machine. Other non-woven manufacturing techniques, such as hydroentangling, melt blown, spun bonded, needle punched and related methods may also be used. However, it is preferred that the substrate be made substantially free of binder or latex and other impurities that may degrade or interact with the solid hypochlorite precipitate. Hydroentrangling manufacturing techniques using high speed water jets are generally preferred due to the high density matrices produced and the high degree of cleanliness of the resulting non-woven articles produced by this method.

Suitable substrates or substrate layers are generally selected from man-made and synthetic construction materials or substrates, preferably including synthetic polymers. For good cleaning, absorption, handling and loading characteristics, it is desirable that the absorbent carrier materials be in the form of fiber, webs or foams of the suitable construction materials.

Suitable forms of employing fibers include woven and non-woven structures. Suitable woven structures include, by way of example and not by way of limitation, meshes, screens, knits, fabrics and other similarly woven structures, of sufficiently high fiber count and strength to be handled by typical machinery and process equipment needed for forming, cutting and packaging the disinfectant articles, preferably when in a dry state. Suitable woven structures include those structures that are of sufficiently high fiber count and strength to be dispensed and handled during use, preferably when in a dry state and/or when in a wetted state.

Suitable woven and non-woven structures are composed of fibers with both sufficient fiber sizes and fiber densities to provide some absorption capacity and enable loading of a sufficient quantity of the disinfectant solution so as to provide for effective treatment of surfaces. Suitable fiber sizes and may vary depending on the choosen application for the substrate with the in situ hypochlorite precipitate. Denier is a weight-per-unit-length measurement of a linear material defined as the number of grams per 9000 meters. For example, in one emboidment standard to larger denier size are preferable because they can improve the stability of the substrates which makes them effective for a longer period of time. In this emboidment, the fibers in the substrate will have about 1.5 to 6.0 denier. In this embodiment, suitable non-woven structures include those structures that are of sufficiently high fiber count and strength to be dispensed from the packaging articles, without significant deformation, tearing or ripping, and handled during use, without unraveling, abrading or tearing, preferably when in a wetted state.

In another embodiment of the invention, smaller fiber sizes, less than 3 denier, or less than 2 deninier, or less and 1 denier, or nanofibers, are preferred. Smaller fiber sizes generally improve absorbency, metering release and provide increased surface area creating more space for hypochlorite precipitate to form. For example, for a substrate used in a wound care application may comprise nanofibers to provide lots of surface area and metered/controlled release of the hypochlorite and optional other actives from the substrate. In an alternative example, a toilet wand cleaning head may employ larger fibers in a hi-loft substrate which are strong fibers which will withstand abrasive cleaning or scrubbing of a toilet bowl. In another exemplary embodiment, a substrate with in situ hypochlorite precipitate that is used for filtration devices may contain trilobal or flat fibers to aid filtration processes and configurations. In essence, the size, shape, composition and arrangement of the fibers in the substrate material may be changed in a variety of different ways to suit a particular application or use.

Suitable substrates employed for constructing the substrate layer comprising the hypohalite precipitate may be provided by a variety of sources, and include all suitable substrates that are hypohalite stable, in that they undergo no significant degradation. That is, suitable substrates that undergo no significant chemical or physical change in structure, properties or form, owing to contact with the disinfectant compositions employed in the present invention, even after extending contact or storage times under representative storage conditions. Preferred are suitable substrates that do not cause significant degradation of the associated or absorbed disinfecting compositions, that is, substrates that do not catalyze or significantly accelerate the decomposition of the associated hypohalite compositions.

Suitable materials of construction generally include synthetic polymer substrates, such as, by way of example and not by way of limitation, polyethylene terephthalate (PET), polyethylene (PE), high density polyethylene (HDPE), low density polyethylene (LDPE), polyvinyl chloride (PVC), chlorinated polyvinylidene chloride (CPVC), polyacrylamide (ACAM), polystyrene (PS), polypropylene (PP), polycarbonate (PC), polyaryletherketone (PAEK), poly(cyclohexylene dimethylene cyclohexanedicarboxylate) (PCCE), poly(cyclohexylene dimethylene terephthalate) (PCTA), poly(cyclohexylene dimethylene terephtalate) glycol (PCTG), polyetherimide (PEI), polyethersulfone (PES), poly(ethylene terephthalate) glycol (PETG), polyketone (PK), poly(oxymethylene); polyformaldehyde (POMF), poly(phenylene ether) (PPE), poly(phenylene sulfide) (PPS), poly(phenylene sulfone) (PPSU), syndiotactic polystyrene (syn-PS), polysulfone (PSU), polytetrafluoroethylene (PTFE), polyurethane (PUR), poly(vinylidene fluoride) (PVDF), polyamide thermoplastic elastomer (TPA), polybutylene (PB), polybutylene terephthalate (PBT), polypropylene terephthalate (PPT), polyethylene naphthalate (PEN), polyhydroxyalkanoate (PHA), poly(methyl)methacrylate (PMMA) and polytrimethylene terephthalate (PTT).

Suitable materials of construction also include copolymers made from the following monomers: polyethylene terephthalate (PET), polyethylene (PE), polypropylene (PP), acrylonitrile-butadiene-styrene (ABS), acrylonitrile-styrene-acrylate (ASA), ethylene-propylene (E/P), ethylene-vinyl acetate (EVAC), methyl methacrylate-acrylonitrile-butadiene-styrene (MABS), methacrylate-butadiene-styrene (MBS), melamine-formaldehyde (MF), melamine-phenol-formaldehyde (MPF), phenol-formaldehyde (PF), styrene-butadiene (SB), styrene-maleic anhydride (SMAH), copolyester thermoplastic elastomer (TPC), olefinic thermoplastic elastomer (TPO), styrenic thermoplastic elastomer (TPS), urethane thermoplastic elastomer (TPU), thermoplastic rubber vulcanisate (TPV), copolymer resins of styrene and acrylonitrile (SAN), styrene butadiene copolymer (SBC) and vinyl acetate-ethylene copolymer (VAE).

In one embodiment of the invention, the entire substrate is substantially free, preferably devoid, of any binders, adhesives, glues tacifiying agents, latex materials or the like. In another embodiment of the invention, at least one fibrous layer of the substrate material which contains the hypochlorite precipitate is substantially free of any binder, adhesives, glues, tacifiying agents, latex materials, or the like. In this embodiment of the invention, binders and adhesives may be used in the substrate as long as they are kept separate from the hypohalite precipitate. Binders, adhesives or the like may be in other layers of the substrate material for the purpose of join layers of materials together, adhering abrasive materials or a variety of other purposes know in the art.

Substantial elimination of binders and latexes, and the like, can be accomplished by pre-washing the dry absorbent carrier in soft, distilled or de-ionized water or other solvents, or by using a substantially binder-free and latex-free process, such as hydroentangling (also known in the art as spunlace technology). More specifically, in the hydroentangling process, a fibrous web is subjected to high-velocity water jets, preferably employing de-ionized, distilled or soft water that entangle the fibers. The non-woven material may then be subjected to conventional drying and wind-up operations, as known to those skilled in the art. Since the hydroentangling process precludes the use of binders, and can be used to wash off at least a portion of the fiber latexes, it is one of the most preferred processes for use in the manufacture of materials of construction of the present invention. Suitable materials of construction that are readily available in commerce include, but are not limited to, the SONTARA® brand of non-woven fabrics produced by Dupont. Representative materials include 100% polyester substrate materials designated SONTARA® 8001, 8005H, 8010 and 8061, and 50% polyester/50% Dacron® blends designated SONTARA® 8100 and including hydrophilically modified 100% polyester substrate material designated SONTARA® 8005H. Additional examples include materials commercially available from Polymer Group Inc, including 100% spunlaced polyester and polypropylene materials designated M001, M022, M040X, CG003, CG005, CG2009, M017, N2006 and T133. Representative materials also include spunlaced 100% polyester materials, designated as 350160 and 10203-003, available from Jacob Holms Industries.

Hypohalite Solution Components

Suitable hypohalite compounds may be provided by a variety of sources, including bleaches that lead to the formation of positive halide ions and/or hypohalite ions, as well as bleaches that are organic based sources of halides, such as chloroisocyanurates, haloamines, haloimines, haloimides and haloamides, or mixtures thereof. These bleaches are all capable of producing hypohalite-bleaching species in situ. Preferred hypohalite bleaches for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chlorosulfamide, N-chloroamines, chlorohydantoins, such as dichlorodimethyl hydantoin and chlorobromo dimethylhydantoin, or mixtures thereof.

In a preferred embodiment the hypohalite composition comprises an alkali metal and/or alkaline earth metal hypochlorite, or mixtures thereof. More preferably, the hypohalite composition comprisies an alkali metal and/or alkaline earth metal hypochlorite selected from the group consisting of sodium hypochlorite, potassium hypochlorite, magnesium hypochlorite, lithium hypochlorite and calcium hypochlorite, and mixtures thereof. Even more preferably, the hypohalite solution comprises sodium hypochlorite.

Hypohalite Precipitate

The hypohalite precipitate is formed when the fibrous substrate is treated with an alkaline earth salt solution and a hypohalite solution and then at least 65% of the liquid phase is removed from the substrate material. The solid hypohalite precipitate forms around the fibers and in the interstices of the fibrous layer. The solid hypohalite precipitate is able to form around the fibers of the fibrous layer because it is formed in situ on the fibrous material. The hypohalite precipitate may be substancially evenly distributed throughout the width of one or more fibrous layers of substrate material. The hypohalite precipitate comprises mixtures and combinations of hypohalite salts.

In one embodiment of the invention, the hypohalite-releasing substrate is a hypochlorite-releasing substrate and the hypohalite precipitate is a hypochlorite precipitate selected from the group consisting of: hypochlorite monohydrate salt, hypochlorite dihydrate salt, hemibasic hypochlorite salt, monobasic hypochlorite salt, dibasic hypochlorite salt, anhydrous hypochlorite salt, and mixtures and combinations thereof.

Cleaning Composition

In one embodiment, the hypohalite-releasing substrate may be impregnated with a cleaning composition. If the hypohalite-releasing substrate is impregnated with a cleaning composition, at least one layer of the substrate material may be 'wet-to-the-touch' while another layer of the substrate may be 'dry-to-the-touch'. In another embodiment, the entire substrate is impregnated with a cleaning composition and the entire substrate is 'dry-to-the-touch'. By 'dry-to-the-touch', it is meant that the substrate is substantially free of water or other solvents in an amount that would make them feel damp or wet-to-the-touch as compared to the touch of a wet substrate, for example a wet cleaning wipe. The cleaning composition may comprise surfactants and additives which are found in a wide variety of cleaning articles. The cleaning composition may be found in the same fibrous layer of the substrate as the hypohalite precipitate or it may be held in a separate layer of the substrate material and it may be separated from the hypohalite precipitate layer by a moisture impermeable material.

Surfactants

Optionally, surfactants suitable for use in this invention are selected from anionic, non-ionic, amphoteric, zwitterionic surfactants and mixtures thereof. It is especially preferred to use a combination of anionic and bleach-stable, non-ionic surfactants. The anionic surfactant is selected from bleach-stable surfactants such as alkali metal alkyl sulfates, secondary alkane sulfonates (also referred to as paraffin sulfonates), alkyl diphenyl ether disulfonates, fatty acid soaps, and mixtures thereof. Such an anionic surfactant will preferably have alkyl groups averaging about 8 to about 20 carbon atoms. In practice, the use of any other anionic surfactant, this does not degrade chemically when in contact with a hypohalite bleaching species, is considered suitable for use in this invention.

An example of a particularly preferred secondary alkane sulfonate is HOSTAPUR SAS, manufactured by Farbwerke Hoechst A.G., Frankfurt, West Germany. Examples of typical alkali metal salts of alkyl benzene sulfonic acids are those manufactured by Pilot Chemical Company sold under the trademark CALSOFT. An example of a typical alkali metal alkyl sulfate is CONCO SULFATE WR, sold by Continental Chemical Company, which has an alkyl group of about 16 carbon atoms. When the electrolyte used is an alkali metal silicate, it is most preferable to include a soluble alkali metal soap of a fatty acid, such as a hexyl to tetradecyl fatty acid soaps. Especially preferred are sodium and potassium soaps of lauric and myristic acid. When used as a component of the inventive cleaning composition, the alkali metal soap of a fatty acid is present in an amount from above zero to about 10 weight percent of the composition.

Examples of preferred bleach-stable, non-ionic surfactants are amine oxides, especially trialkyl amine oxides, as represented in the formula expression RR'R"NO, in which R' and R" may be alkyls of 1 to 3 carbon atoms and are most preferably methyls, and R is an alkyl of about 10 to 20 carbon atoms. When R' and R" are both methyl and R is alkyl averaging about 12 carbon atoms, the structure for dimethyldodecylamine oxide, a particularly preferred amine oxide, is obtained. Representative examples of these particular types of bleach-stable, non-ionic surfactants include the dimethyldodecylamine oxides sold under the trademark AMMONYX LO by Stepan Chemical. Yet other preferred amine oxides are those sold under the trademark BARLOX by Lonza, CONCO XA sold by Continental Chemical Company, AROMAX sold by Akzo, and SCHERCAMOX, sold by Scher Brothers, Inc. These amine oxides preferably have main alkyl chain groups averaging about 10 to about 20 carbon atoms. Other types of suitable surfactants include amphoteric surfactants such as, for example, betaines, imidazolines and certain quaternary phosphonium and tertiary sulfonium compounds.

It is suitable to use one or more surfactants in the inventive cleaning substrates. The surfactants may be incorporated in the same layer of substrate material as the hypochlorite precipitate or alternatively surfactants may be included in separate layer or layers of the substrate where it may be separated from the layer containing the hypochlorite precipitate. In the inventive composition, total surfactant, when present, is included in an amount ranging from about 0.001 to about 20 weight percent of the cleaning composition, preferably in an amount ranging from about 0.01 to about 5 weight percent of the composition. For reduced surface residue and to decrease the tendency of the compositions to contribute to excess foaming, residual filming or streaking, and particularly for use on glossy or shiny surfaces, total surfactant, when present, is included in an amount most preferably from about 0.01 to about 1.0 weight percent of the composition.

Optionally, an additional co-surfactant may be added to the disinfectant composition of this invention. The bleach stable anionic surfactants include alkali metal alkyl sulfates, alkylarylsulfonates, primary and secondary alkane sulfonates (also referred to as paraffin sulfonates), alkyl diphenyloxide disulfonates, and mixtures thereof. The anionic surfactants have alkyl groups preferably averaging about 8 to 20 carbon atoms. The alkyl arylsulfonic acid salts of preference are linear alkylbenzene sulfonates, known as LAS's. Typical LAS's have C 8-16 alkyl groups, non-limiting examples of which include Stepan Company's Biosoft and Pilot Chemical Company's Calsoft. Still further suitable surfactants are the alkyldiphenylether disulfonates (also called alkyldiphenyloxide disulfonates), such as, by way of example only, those sold by Dow Chemical Company under the name "Dowfax," e.g., Dowfax 3B2. Still other potentially suitable anionic surfactants include alkali metal alkyl sulfates such as Conco Sulfate WR, sold by Continental Chemical Company, which has an alkyl group of about 16 carbon atoms; and secondary alkane sulfonates such as Hostapur SAS, manufactured by Farbwerke Hoechst AG.

Additives

The disinfectant composition of the present invention may optionally be formulated to include further adjuncts, for example, sequestrants, chelants, hydrotropes, effervescent materials, thickening agents, rheology modifiers, fragrances, coloring agents, pigments (e.g., ultramarine blue), bleach-stable dyes (e.g., anthraquinone dyes), whiteners, including the optional surfactants, solvents, chelating agents and builders, which enhance performance, stability or aesthetic appeal of the composition. Generally, such adjuncts may be added in relatively low amounts, e.g., each from about 0.001 to about 5.0 weight percent of the composition.

Optionally, sequestering agents are suitable for use in the inventive c Sequestering agents are selected from the group consisting of metal chelators, metal sequestrants and ion exchange materials known in the art. Preferably, metal chelators and metal sequestrants are selected from the group consisting of the alkali and alkaline earth salts of the phosphates, phosphonates, borates, silicates, polyfunctionally-substituted aromatic chelating agents, ethylenediamine tetra-acetate (EDTA) and ethylenediamine-N,N'-disuccinic acids, or mixtures thereof. Preferred sequestering agents are the silicates and ethylenediamine tetra-acetate.

Optionally, polyfunctionally-substituted aromatic chelating agents may also be useful in the bleaching compositions herein. See U.S. Pat. No. 3,812,044, issued May 21, 1974, to Connor et al. Preferred compounds of this type in acid form are dihydroxydisulfobenzenes such as 1,2-dihydroxy-3,-5-disulfobenzene. A preferred biodegradable chelating agent for use herein is ethylene diamine N,N'-disuccinic acid, or alkali metal, or alkaline earth, ammonium or substituted ammonium salts thereof or mixtures thereof.

The substrate or cleaning composition loaded onto the substrate may comprise materials that effervesce when combined with water. The materials may be within a water-soluble, water-insoluble, or water-dispersible pouch to slow the effervescent action or to protect the composition from premature hydration. The materials may comprise a polymeric agent to slow the effervescence. One component of the effervescent materials may be an acidic material. Suitable for this purpose are any acids present in dry solid form. Suitable for this purpose are C2-20 organic mono- and poly-carboxylic acids such as alpha- and beta-hydroxycarboxylic acids; C2-20 organophosphorus acids such as phytic acid; C2-20 organosulfur acids such as toluene sulfonic acid; and peroxides such as hydrogen peroxide or materials that generate hydrogen peroxide in solution. Typical hydroxycarboxylic acids include adipic, glutaric, succinic, tartaric, malic, maleic, lactic, salicylic and citric acids as well as acid forming lactones such as gluconolactone and gluccrolactone. A suitable acid is citric acid. Also suitable as acid material may be encapsulated acids. Typical encapsulating material may include water-soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7. These acids may also have a pH of less than 6.5 or less than 5. These acids may be at 25° C. in solid form, i.e. having melting points greater than 25° C. Concentrations of the acid should range from about 0.5 to about 80%, or from about 10 to about 65%, or from about 20 to about 45% by weight of the total composition.

Another component of the effervescent materials may be an alkaline material. The alkaline material may a substance that can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). An example of the alkaline material is sodium or potassium bicarbonate. Amounts of the alkaline material may range from about 1 to about 80%, or from about 5 to about 49%, or from about 15 to about 40%, or from about 25 to about 35% by weight of the total composition.

When the cleaning composition or substrate comprises effervescent materials, then the composition may comprise no more than 5%, or no more than 3.5%, or no more than 1% water by weight of the total composition. Water of hydration is not considered to be water for purposes of this calculation. However, water of hydration may be preferred or eliminated. The combined amount of acidic and alkaline materials may be greater than 1.5%, or from about 40 to about 95%, or from about 60 to about 80% by weight of the total composition.

The optional hydrotropes are preferably selected from short chain alkylarylsulfonates, salts of benzoic acid, benzoic acid derivatives (such as chlorobenzoic acid), and mixtures thereof. As used herein, aryl includes, without limitation, at least benzene, naphthalene, xylene, cumene and similar aromatic nuclei. These aryl groups can be substituted with one or more substituents known to those skilled in the art, e.g., halo (chloro, bromo, iodo, fluoro), nitro, or C 1-4 alkyl or alkoxy. Most preferred is sodium xylene sulfonate (such as Stepanate SXS, available from Stepan Company).

By way of example, a fragrance such as a fragrance commercially available from International Flavors and Fragrance, Inc., may be included in the inventive composition in an amount from about 0.01 to about 0.5 weight percent of the composition. Dyes and pigments may be included in small amounts in the composition of the present invention. Examples of widely used, suitable pigments include ultramarine blue (UMB) and copper phthalocyanines Solvents may also be added to the inventive compositions to enhance cleaning and/or disinfectant efficacy of the compositions. The solvents maybe held separately from the hypohalite precipitate layer of the substrate. Alternatively, low levels of solvents, less than 20%, less than 10% or less than 5%, maybe held in the substrate in the same layers as the hypohalite precipitate. For example, certain less water soluble or dispersible organic solvents, some of which are advantageously stable in the presence of hypochlorite bleach, may be included. These bleach-stable solvents include those commonly used as constituents of proprietary fragrance blends, such as terpenes and essential oils, and their respective derivatives.

The terpene derivatives suitable for the present invention include terpene hydrocarbons with a functional group. Effective terpenes with a functional group include, but are not limited to, alcohols, ethers, esters, aldehydes and ketones. Representative examples of each of the above-mentioned terpenes with a functional group include, but are not limited to, the following: (1) terpene alcohols, including, for example, verbenol, transpinocarveol, cis-2-pinanol, nopol, isoborneol, carbeol, piperitol, thymol, alpha-terpineol, terpinen-4-ol, menthol, 1,8-terpin, dihydroterpineol, nerol, geraniol, linalool, citronellol, hydroxycitronellol, 3,7-dimethyl octanol, dihydromyrcenol, beta-terpineol, tetrahydro-alloocimenol and perillalcohol; (2) terpene ethers and esters, including, for example, 1,8-cineole, 1,4-cineole, iso-bornyl methylether, rose pyran, alpha-terpinyl methyl ether, menthofuran, trans-anethole, methyl chavicol, allocimene diepoxide, limonene mono-epoxide, iso-bornyl acetate, nopyl acetate, alpha-terpinyl acetate, linalyl acetate, geranyl acetate, citronellyl acetate, dihydro-terpinyl acetate and nerol acetate; and (3) terpene aldehydes and ketones, including, for example, myrtenal, campholenic aldehyde, perillaldehyde, citronellal, citral, hydroxy citronellal, camphor, verbenone, carvenone, dihydrocarvone, carvone, piperitone, menthone, geranyl acetone, pseudo-ionone, alpha-ionone, beta-ionone, iso-pseudo-methyl ionone, normal-pseudo-methyl ionone, iso-methyl ionone and normal-methyl ionone. Terpene hydrocarbons with functional groups which appear suitable for use in the present invention are discussed in substantially greater detail by Simonsen and Ross, The Terpenes, Volumes I-V, Cambridge University Press, 2nd Ed., 1947, which is incorporated herein in entirety by this reference. See also, commonly assigned U.S. Pat. No. 5,279,758, issued to Choy on Jan. 18, 1994, which is incorporated herein in entirety by this reference.

Cleaning Head

The present invention is directed to a method for forming a solid hypohalite precipitate, preferably a hypochlorite precipitate, on a fibrous substrate and composition formed thereof. In one embodiment of the invention, the fibrous substrate with a solid hypochlorite precipitate may be a cleaning head for various household cleaning tools. Such household cleaning tools include but are not limited to, toilet bowl cleaning heads, bath and shower cleaning heads, mop heads, dishwashing tool heads, and the like. In one aspect of the cleaning head embodiment of the invention, it is desirable to have at least one hi-loft layer of the cleaning head. The hi-loft layer of the cleaning head may be desirable because it will help provide quick release of the soild hypochlorite material when it is exposed to a fluid. For example, in a cleaning head used for cleaning a toilet bowl, the hi-loft layer may allow the substrate to quickly and effectively release they hypochlorite precipitate when wetted to efficiently clean and disinfect the toilet bowl.

The quick release of hypochlorite is essential for some applications such as toilet bowl cleaning and shower cleaning because the user quickly dips the cleaning head in water and then immediately begins cleaning the desired surface. Therefore for the hypochlorite and/or surfactants must be able to release quickly from the cleaning head to adequately disinfect the surface being cleaned. The present invention provides a few significant advantages over the prior art in accomplishing quick release because the hypochlorite containing substrate may be substantially free of binders, adhesives, glue, latex, tacifiying agents and the like. In addition, the present invention comprises solid hypochlorite precipitates, such as hypochlorite dihydrate salt, which have quick dissolution rates. In addition, unlike traditional solid hypochlorite substrates where the solid particles are attached to the surface the solid hypochlorite precipitate may be evenly distributed throughout a layer of substrate material or throughout the entire substrate which contributes to a more even release rate of hypochlorite. In the case of surfactants, quick but sustained release is desirable so that there is sufficient foam for the consumer to last throughout the entire cleaning surface. It is also desirable to have sustained release of the hypohalite component because it will allow the substrate to disinfect the entire surface that the user desires to clean.

In another embodiment of the invention, the cleaning head may have more than one layer of fibrous materials. In the case of a cleaning head for a household cleaning tool it may be desirable to have a scrubby layer as the top fibrous layer of the cleaning head. The scrubby layer may comprise an abrasive material comprising: abrasive particulates, abrasive fibers, bristles, foam, and any other abrasive materials know in the art. The abrasive material may be formed as a separate layer of the cleaning head or may be formed on the surface of another layer of the cleaning head.

The cleaning head may have other layers of fibrous materials including but not limited to an absorbent layer, a fluid impervious layer and a tool attachment layer. The absorbent layer may include any suitable fibrous absorbent material. A fluid impervious layer may be located in between various layers of the cleaning head to prevent the solid hypochlorite precipitate from being exposed to another layer of fibrous material containing a fluid or containing an active that is reactive with the solid hypochlorite precipitate. In one embodiment, the fluid impervious layer is adjacent to the tool attachment layer to prevent the tool attachment layer from becoming saturated with fluid which could weaken its attachment strength to the rest of the tool assembly. The attachment layer could be a velco, adhesive, hook and loop, button, mating snap, and any other suitable attachment means. The tool assembly may be a simple handle, an elongated handle or pole or an interchangeable cleaning head fitment which may be attached to a wide variety of different mops, brushes, vacuums, brooms, and other suitable household cleaning tools.

Suitable non-limiting examples of household cleaning tools may be found in the following references. One example of a suitable cleaning head is described in published Application 2005/0217698, which was filed Apr. 1, 2004, entitled "Ergonomic Cleaning Pad", and which is hereby incorporated by reference. In another embodiment of the invention, the cleaning implement comprises the tool assembly disclosed in U.S. Pat. No. 7,065,825, entitled "Cleaning Tool with Gripping Assembly for a Disposable Scrubbing Head", filed Jun. 23, 2003, which is hereby incorporated by reference. In another embodiment of the invention, the cleaning implement comprises the tool assembly disclosed in U.S. Pat. No. 6,953,299, entitled "Cleaning Implement with Interchangeable Tool Heads", filed Jan. 27, 2004, which is hereby incorporated by reference. In another embodiment of the invention, the cleaning implement comprises the tool assembly disclosed in U.S. Pat. No. 7,065,838, entitled "Locking Segmented Cleaning Implement Handle", filed May 19, 2004, hereby incorporated by reference.

In another embodiment of the invention, the cleaning implement comprises an elongated shaft having a handle portion on one end thereof. The tool assembly may further include a gripping mechanism that is mounted to the shaft to engage the removable cleaning substrate. Examples of suitable cleaning implements are found in US2003/0070246 to Cavalheiro; U.S. Pat. No. 4,455,705 to Graham; U.S. Pat. No. 5,003,659 to Paepke; U.S. Pat. No. 6,485,212 to Bomgaars et al.; U.S. Pat. No. 6,290,781 to Brouillet, Jr.; U.S. Pat. No. 5,862,565 to Lundstedt; U.S. Pat. No. 5,419,015 to Garcia; U.S. Pat. No. 5,140,717 to Castagliola; U.S. Pat. No. 6,611,986 to Seals; US2002/0007527 to Hart; and U.S. Pat. No. 6,094,771 to Egolf et al. The cleaning implement may have a hook, hole, magnetic means, canister or other means to allow the cleaning implement to be conveniently stored when not in use.

Housing Systems and Packaging Materials

Suitable packaging materials may be provided by a variety of sources, and include all suitable materials that are moisture impermeable and preferably heat resistant. It is preferred that the housing or packaging materials be hypohalite stable, in that they undergo no significant degradation. That is, the packaging materials undergo no significant chemical or physical change in structure, properties or form, owing to contact with the hypohalite compositions employed in the present invention. Suitable packaging materials include those materials common to the art.

Housing systems include both individually packaged disinfectant wipes and bulk packaged one or more disinfectant wipes or other suitable disinfecting articles. The housing system preferably comprises a sealable container, which is substantially impervious to both liquid and gas. The term "container", refers to, but is not limited to, packets containing one or more individual disinfectant wipes and bulk dispensers, such as canisters, tubs and jars, which dispense one disinfectant wipe at a time, and further feature suitable means to reseal the bulk dispenser between uses to preserve the integrity of the disinfecting articles. One example is a cylindrical canister dispenser that hosts a roll of individual wipes, separated by perforations to permit the tearing off of individual wipes for use. Such dispenser is conveniently gripped by the user and held in position while the user removes a wipe. Preferred are dispensers featuring a resealable dispensing cap and orifice (See, e.g., Chong, U.S. Pat. No. 6,554,156, of common assignment and incorporated herein by reference thereto) that dispenses individual wipes from a roll and retains the next wipe in a ready-to-dispense position, yet allows sealing of the dispensing cap to close the container against the environment when not in use. A further example, within the scope of the present invention, is to package individual wipes in a non-linked manner, in a dispenser permitting their removal one at a time, as is the case with many wipe/dispenser combinations known in the art.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

We claim:

1. A process for making a hypochlorite-releasing substrate comprising the steps of:
    a. providing at least one layer of fibrous material comprising synthetic fibers;
    b. treating the fibrous layer to an effective amount of an aqueous alkaline earth salt solution,
    c. treating the fibrous layer with an effective amount of a hypochlorite solution, and
    d. allowing the aqueous alkaline earth salt solution combine with the hypochlorite solution to form a solid hypochlorite precipitate around the fibers in the fibrous material and a liquid phase, and
    e. removing at least 65% of the liquid phase from the substrate.

2. The process for making a hypochlorite-releasing substrate according to claim 1, wherein the alkaline earth salt solution is selected from the group consisting of: magnesium chloride, calcium chloride, calcium hydroxide, magnesium hydroxide and any mixtures or combinations thereof.

3. The process for making a hypochlorite-releasing substrate according to claim 1, wherein the hypochlorite solution comprises compounds selected from the group consisting of: sodium hypochlorite, potassium hypochlorite, lithium hypochlorite, calcium hypochlorite, magnesium hypochlorite, hypochlorous acid, and any mixtures or combinations thereof.

4. The process for making a hypochlorite-releasing substrate according to claim 1, wherein the fibrous material comprises fibers selected from the group consisting of: natural cellulose, regenerated cellulose, polyester, acrylic, nytril, cellulose ester, olefin, vinyl and any combinations or mixtures thereof.

5. The process for making a hypochlorite-releasing substrate according to claim 1, wherein the fibers are selected from the group consisting of: polypropylene, polyethylene, polyester and any mixtures or combinations thereof.

6. The process for making a hypochlorite-releasing substrate according to claim 1, wherein the solid hypochlorite precipitate contains salts selected from the group consisting of: hypochlorite monohydrate salt, hypochlorite dihydrate salt, hemibasic hypochlorite salt, monobasic hypochlorite salt, dibasic hypochlorite salt, anhydrous hypochlorite salt, and mixtures or combinations thereof.

7. The process for making a hypochlorite-releasing substrate according to claim 1 wherein the substrate comprises two or more layers of fibrous materials.

8. The process for making a hypochlorite-releasing substrate according to claim 1 wherein the solid hypochlorite precipitate forms around the fibers in the fibrous material.

9. The process for making a hypochlorite-releasing substrate according to claim 1 wherein the solid hypochlorite precipitate adheres to the substrate without the aid of binders, adhesives, glues, or tackifying agents.

10. The process for making a hypochlorite-releasing substrate according to claim 9, further comprising a step of adding bleach stable surfactants to at least one fibrous layer.

11. A process for making a hypochlorite-releasing substrate comprising the steps of:
    a. providing a first layer of fibrous material comprising fibers selected from the group consisting of: natural cellulose, regenerated cellulose, polyester, acrylic, nytril, cellulose ester, olefin, vinyl and any combinations or mixtures thereof,
    b. treating the first fibrous layer to an effective amount of an aqueous alkaline earth salt solution,
    c. providing a second layer of fibrous material comprising synthetic fibers;
    d. treating the second fibrous layer with an effective amount of a hypochlorite solution, and
    e. contacting the first layer of fibrous material with the second layer of fibrous material and allowing the aqueous alkaline earth salt solution combine with the hypochlorite solution to form a solid hypochlorite precipitate.

12. The process for making a hypochlorite-releasing substrate according to claim 11, wherein the alkaline earth salt solution is selected from the group consisting of: magnesium chloride, calcium chloride, calcium hydroxide, magnesium hydroxide and any mixtures or combinations thereof.

13. The process for making a hypochlorite-releasing substrate according to claim 11, wherein at least one of the fibrous material layers is selected from the group consisting of: spunbond, meltblown, spunbond meltblown spunbond, carded, wetlaid, airlaid, thermalbonded, hydroentangled, through-air bonded, needled, chemical bonded, and combinations thereof.

14. The process for making a hypochlorite-releasing substrate according to claim 11, wherein the fibers from at least one of the fibrous layers are selected from the group consisting of: polypropylene, polyethylene, polyester and any mixtures or combinations thereof.

15. The process for making a hypochlorite-releasing substrate according to claim 11 further comprising the step of adding an additive selected from the group consisting of: emulsifiers, pH adjusters, silicones, non-ionic surfactants, cationic surfactants, amphoteric surfactants, zwitterionic surfactants, anionic surfactants, soil release agents, soil release polymers, antistatic agents, fragrances, fragrance extenders, antimicrobial actives, preservatives, dyes, colorants, viscosity control agents, antifoaming agents, pearlizing agents, opacifying agents, antioxidants, sunscreens, dye transfer inhibitors, dye fixative agents, dispersants, chlorine scavengers, wetting agents, electrolytes, enzymes, brighteners, heavy metal chelating agents, fabric softener actives, soil suspending agents, soil release agents, and mixtures thereof.

16. A process for making a hypochlorite-releasing substrate comprising the steps of:
 a. providing at least one layer of fibrous material comprising synthetic fibers;
 b. treating the fibrous layer to an effective amount of an aqueous alkaline earth salt solution,
 c. treating the fibrous layer with an effective amount of a hypochlorite solution, and
 d. allowing the aqueous alkaline earth salt solution combine with the hypochlorite solution to form a solid hypochlorite precipitate around the fibers in the fibrous material and a liquid phase, and
 e. adding at least one surfactant to the substrate.

17. The process of making a hypochlorite-releasing substrate according to claim 16, wherein the substrate comprises two or more layers of materials.

18. The process of making a hypochlorite-releasing substrate according to claim 16, wherein the surfactant is added to the substrate as a liquid solution which co-precipitates as the hypochlorite precipitate forms on the substrate.

19. The process of making a hypochlorite-releasing substrate according to claim 17, wherein the hypochlorite precipitate resides in a fibrous layer and the surfactant resides in a separate layer of the substrate.

20. The process of making a hypochlorite-releasing substrate according to claim 16, wherein the surfactant is selected from the group consisting of: secondary alkyl sulfates, amine oxides, caustic neutralized fatty acids, and any combinations thereof.

* * * * *